United States Patent
Yamaguchi et al.

(10) Patent No.: US 6,436,243 B1
(45) Date of Patent: Aug. 20, 2002

(54) PROCESS FOR RECOVERING N-VINYL-2-PYRROLIDONE

(75) Inventors: Yoshinari Yamaguchi, Himeji; Hitoshi Yano, Suita; Akira Kurusu, Kyoto; Yuuji Shimasaki, Otsu, all of (JP)

(73) Assignee: Nippon Shokubai Co LTD, Osaka (JP)

( * ) Notice: Subject to any disclaimer, the term of this patent is extended or adjusted under 35 U.S.C. 154(b) by 0 days.

(21) Appl. No.: 09/690,846

(22) Filed: Oct. 18, 2000

(30) Foreign Application Priority Data

Oct. 22, 1999 (JP) .......................................... 11-301423

(51) Int. Cl.⁷ .................... B01D 3/42; C07D 207/267
(52) U.S. Cl. ................ 203/2; 203/14; 203/71; 548/552; 548/555
(58) Field of Search ................ 203/2, 73, 71, 203/14, 100; 548/555, 552, 543, 551

(56) References Cited

U.S. PATENT DOCUMENTS 2,669,570 A * 2/1954 Schnizer ...................... 548/552
2,775,599 A    12/1956 Puetzer et al.
5,625,076 A    4/1997  Shimasaki et al.
5,951,828 A    9/1999  Winter et al.

FOREIGN PATENT DOCUMENTS

GB    717799    11/1954
JP    8141402   6/1996

OTHER PUBLICATIONS

Database Chemabs 'Online', Chemical Abstracts Service, Kirsh, Yu. E. et al. No. SU 670 568, Jun. 30, 1979.
Database Chemabs 'Online', Chemical Abstracts Service, Kirsh, Yu. E. et al. No. SU 582 247, Nov. 30, 1977.

* cited by examiner

Primary Examiner—Virginia Manoharan
(74) Attorney, Agent, or Firm—Sherman & Shalloway

(57) ABSTRACT

A process for recovering N-vinyl-2-pyrrolidone is provided which allows to recover N-vinyl-2-pyrrolidone efficiently and steadily and in high purity by continuous distillation from a mixed liquid containing N-vinyl-2-pyrrolidone, N-(2-hydroxyethyl)-2-pyrrolidone, compounds having a higher boiling point than N-vinyl-2-pyrrolidone and water. The process includes continuously distilling the mixed liquid using a distilling column, controlling the temperature of the bottom liquid of the distilling column at 180° C. or less.

6 Claims, 1 Drawing Sheet

US 6,436,243 B1

PROCESS FOR RECOVERING N-VINYL-2-PYRROLIDONE

TECHNICAL FIELD TO WHICH THE INVENTION PERTAINS

Figure 1:
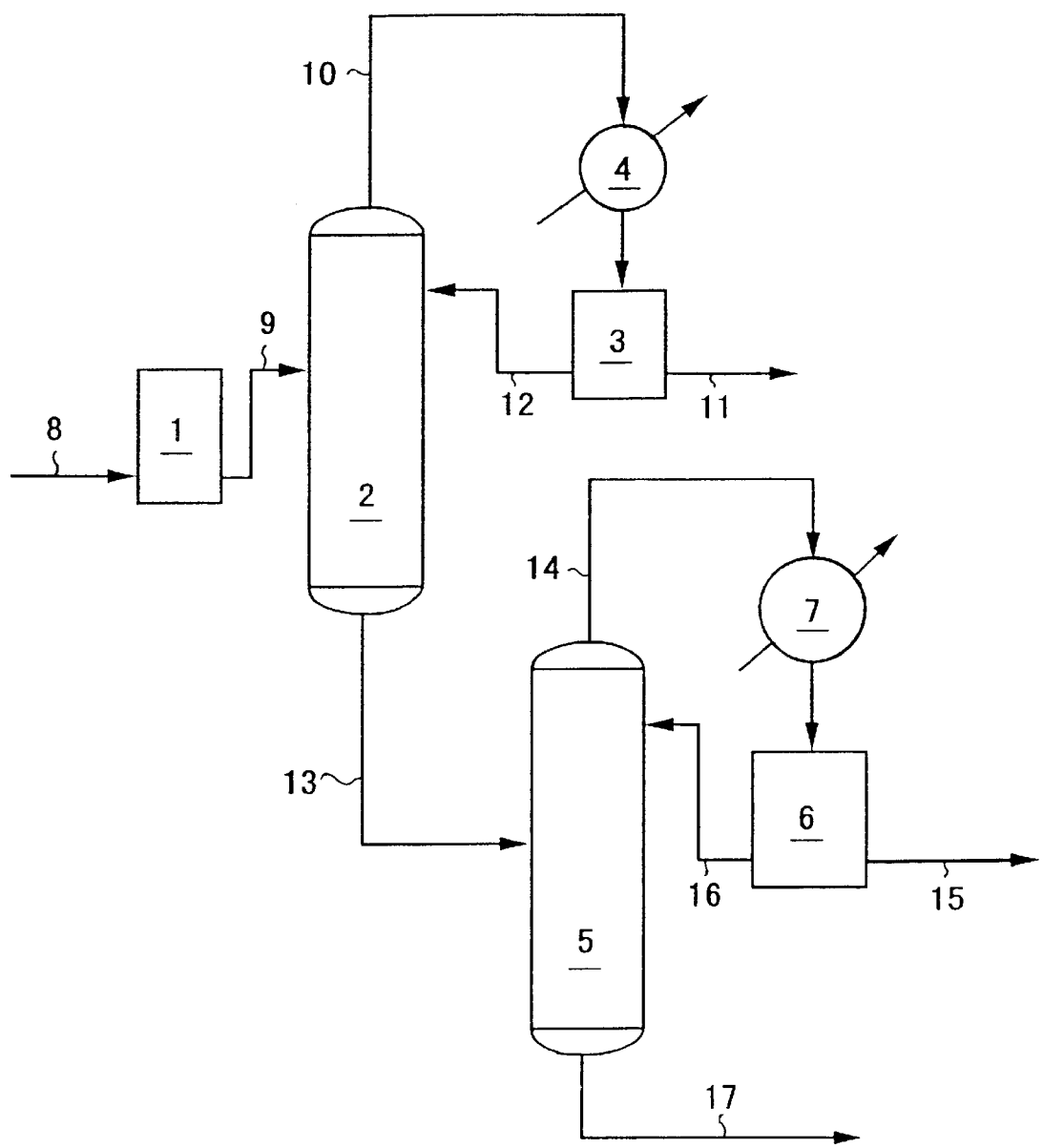

This invention relates to a process for recovering N-vinyl-2-pyrrolidone. N-vinyl-2-pyrrolidone is a useful compound as a raw material monomer for preparing poly-N-vinyl-2-pyrrolidone having wide uses in the fields of medicine, food additives, personal care products, etc.

Prior Art

N-vinyl-2-pyrrolidone has been industrially manufactured by the Reppe process wherein 2-pyrrolidone and acetylene are reacted in a liquid phase under pressure in the presence of an alkali catalyst. However, the Reppe process has various problems, for example that there is a danger that acetylene causes explosion under high pressures, the catalyst preparation step is complicated for preventing the lowering of reaction yield and reaction control such as the control of 2-pyrrolidone conversion is complicated.

Therefore, a preparation process of N-vinyl-2-pyrrolidone not using acetylene as a raw material has been desired, and, for example, various processes have been tried using as a raw material N-(2-hydroxyethyl)-2-pyrrolidone obtained in a good yield by reaction of γ-butyrolactone with monoethanolamine.

For example, there have been proposed a process which comprises dehydrochlorinating N-(2-chloroethyl)-2-pyrrolidone obtained by reaction of N-(2-hydroxyethyl)-2-pyrrolidone with octynyl chloride (U.S. Pat. No. 2,775,599), a process which comprises removing acetic acid from the acetic ester intermediate obtained by reaction of N-(2-hydroxyethyl)-2-pyrrolidone with acetic anhydride, etc. However, since these via intermediate processes have problems that the auxiliary raw material equivalent to N-(2-hydroxyethyl)-2-pyrrolidone is necessary, and more over, intermediate preparation costs a great deal and a large amount of by-products derived from the auxiliary raw material are formed, these cannot be said to be excellent production processes from the industrial viewpoint.

Thus as a process for solving the problems is proposed in Japanese Laid-open Patent Publication No. 8-141402 a process of preparing N-vinyl-2-pyrrolidone by intramolecularly dehydrating N-(2-hydroxyethyl)-2-pyrrolidone in a vapor phase in the presence of a catalyst. In the production process, the raw material N-(2-hydroxy-ethyl)-2-pyrrolidone is easy to get and inexpensive because it is prepared in a good yield by reaction of γ-butyrolactone with monoethanolamine. Further in the production process, no raw material other than N-(2-hydroxyethyl)-2-pyrrolidone is needed, and moreover, the reaction selectivity can be increased by appropriately selecting the kind of catalyst and reaction conditions.

The condensate formed by the reaction in the production process is a mixed liquid having a complicated composition comprising the desired product N-vinyl-2-pyrrolidone, a by-product water, 2-pyrrolidone as a decomposition product of N-(2-hydroxyethyl)-2-pyrrolidone and the unreacted raw material N-(2-hydroxyethyl)-2-pyrrolidone, etc., but there is no disclosure in the above official gazette about a process for recovering N-vinyl-2-pyrrolidone from this mixed liquid in high purity.

Problem to be Solved by the Invention

N-vinyl-2-pyrrolidone is known to be radically polymerized or thermally decomposed by heating and hydrolyzed in the presence of water. Therefore, when N-vinyl-2-pyrrolidone is recovered by a distillation operation from the condensate formed by the reaction in the process of the official gazette, etc., there arises a problem depending on the distillation condition, for example that the recovery percentage of N-vinyl-2-pyrrolidone is lowered by thermal polymerization or thermal decomposition thereof, or polymers are accumulated in the equipment to bring about apparatus troubles.

Thus the object of the invention lies in solving the so far found problem, namely providing a process for recovering N-vinyl-2-pyrrolidone which makes it possible to recover chemically unstable N-vinyl-2-pyrrolidone efficiently and steadily and in high purity by continuous distillation from a mixed liquid having a complicated distillation composition containing N-vinyl-2-pyrrolidone, N-(2-hydroxyethyl)-2-pyrrolidone and water.

Means for Solving the Problem

The present inventors have vigorously studied for providing a recovery process of N-vinyl-2-pyrrolidone, ans as a result they have found that in recovering N-vinyl-2-pyrrolidone by continuously distilling a mixed liquid containing N-vinyl-2-pyrrolidone, N-(2-hydroxyethyl)-2-pyrrolidone, compounds having a higher boiling point than N-vinyl-2-pyrrolidone and water, thermal polymerization and thermal decomposition of N-vinyl-2-pyrrolidone can be inhibited and N-vinyl-2-pyrrolidone can be recovered efficiently and steadily and in high purity by controlling the temperature of the bottom liquid of the distilling column.

Thus, according to the invention is provided in a process for recovering N-vinyl-2-pyrrolidone by continuously distilling a mixed liquid containing N-vinyl-2-pyrrolidone, N-(2-hydroxyethyl)-2-pyrrolidone, compounds having a higher boiling point than N-vinyl-2-pyrrolidone and water using a distilling column, the improvement comprising carrying out the distillation controlling the temperature of the bottom liquid of the distilling column to 180° C. or less to make water distill as the distillate, and, on the other hand, withdrawing the bottom residue comprising N-vinyl-2-pyrrolidone, N-(2-hydroxyethyl)-2-pyrrolidone and the compounds having a higher boiling point than N-vinyl-2-pyrrolidone.

It is preferred to continuously distill the bottom residue withdrawn from the distilling column (the first distilling column) using a second distilling column to make N-vinyl-2-pyrrolidone distill as the distillate, and, on the other hand, withdraw the bottom residue comprising N-(2-hydroxyethyl)-2-pyrrolidone and the compounds having a higher boiling point than N-vinyl-2-pyrrolidone.

It is preferred to operate the second distilling column controlling the temperature of the bottom liquid to 230° C. or less.

The process of the invention is particularly useful when the mixed liquid fed for distillation, namely the mixed liquid comprising N-vinyl-2-pyrrolidone, N-(2-hydroxyethyl)-2-pyrrolidone, the compounds having a higher boiling point than N-vinyl-2-pyrrolidone and water is a liquid obtained by cooling collecting the vapor phase dehydration reaction product of N-(2-hydroxyethyl)-2-pyrrolidone.

Mode for Carrying out the Invention

The liquid as the object of distillation operation in the recovery process of N-vinyl-2-pyrrolidone according to the invention is a mixed liquid containing N-vinyl-2- pyrrolidone, N-(2-hydroxyethyl)-2-pyrrolidone, the compounds having a higher boiling point than N-vinyl-2-pyrrolidone and water, as hereinbefore described. Such a mixed liquid can, for example, be obtained readily by the production process disclosed in Japanese Laid-open Patent Publication No. 8-141402 or the like. Specifically, a liquid collected by cooling an N-vinyl-2-pyrrolidone-containing product obtained by intramolecularly dehydrating N-(2-hydroxyethyl)-2-pyrrolidone in a vapor phase in the presence of a catalyst is mentioned, but no particular limitation thereto is made.

As the compounds having a higher boiling point than N-vinyl-2-pyrrolidone, there can specifically mentioned, besides 2-pyrrolidone, tar-like substances such as the dimer of N-vinyl-2-pyrrolidone, but no particular limitation thereto is made.

When the mixed liquid containing N-vinyl-2-pyrrolidone, N-(2-hydroxyethyl)-2-pyrrolidone, compounds having a higher boiling point than N-vinyl-2-pyrrolidone and water is continuously distilled in the first distilling column, it is pertinent that the temperature of the bottom liquid is 180° C. or less, preferably 165° C. or less. In this apparatus, water distills and is removed and N-vinyl-2-pyrrolidone is withdrawn as the bottom residue. Since when the temperature of the bottom liquid is more than 180° C., thermal polymerization or thermal decomposition of N-vinyl-2-pyrrolidone contained in the bottom liquid is accelerated, the recovery percentage of N-vinyl-2-pyrrolidone is lowered. The object can be accomplished, for example by operating the first distilling column under a reduced pressure of $2.66 \times 10^4$ Pa (200 mmHg) or less, preferably $1.99 \times 10^4$ Pa (150 mmHg) or less, although the value of the reduced pressure also depends on the composition of the mixed liquid to be distilled.

It is preferable to further continuously distill the bottom residue of the first distilling column in another distilling column (second distilling column). In this occasion, it is pertinent that the temperature of the bottom liquid of the second distilling column is 230° C. or less, preferably 210° C. or less. When the temperature of the bottom liquid is more than 230° C., dangers increase such as lowering of the recovery percentage due to thermal polymerization or thermal decomposition of N-vinyl-2-pyrrolidone and lowering of plate efficiency or column clogging due to adhesion of the polymer. In order to avoid these dangers, the pressure operable at 230° C. or less is usually $1.33 \times 10^4$ Pa (100 mmHg) or less, preferably $0.66 \times 10^4$ Pa (50 mmHg) or less, although the pressure is varied depending on the composition of the liquid to be distilled.

Distilling columns used in the invention are not particularly limited in their types, but it is pertinent to use fractionating columns such as plate columns or packed columns. The plate number of the column can appropriately be selected in accordance with the composition of the distillation liquid and the reflux ratio, but is usually on the order of a theoretical plate number of 3 to 30.

The process of the invention of continuously recovering N-vinyl-2-pyrrolidone from a mixed liquid containing N-vinyl-2-pyrrolidone, N-(2-hydroxyethyl)-2-pyrrolidone, compounds having a higher boiling point than N-vinyl-2-pyrrolidone and water is described on its preferred embodiments as follows.

FIG. 1 of the attached drawings is a block drawing showing an example of distilling apparatuses fit to be used for recovery of N-vinyl-2-pyrrolidone according to the process of the invention.

The distilling apparatus is composed of a tank 1, a multistage continuously distilling column (first distilling column) 2, a distillation tank 3, a condenser 4, a multistage continuously distilling column (second distilling column) 5, a distillation tank 6, a condenser 7, etc.

A predetermined amount of the mixed liquid is constantly stored inside the tank 1. The tank 1 is connected with the middle plate section of the continuously distilling column 2 via a pipeline 9, and connected with an N-vinyl-2-pyrrolidone-preparing apparatus or a mixed liquid tank (these are not illustrated) via a pipeline 8. The "middle plate section" referred to in the specification means intermediate plates excluding the highest plate and the lowest plate in a distilling column.

A mixed liquid to be used for distillation according to the process of the invention is continuously fed into the tank 1 from the N-vinyl-2-pyrrolidone-preparing apparatus or the mixed liquid-feeding tank. The mixed liquid is continuously fed from the tank 1 to the middle plate section of the continuously distilling column 2 via the pipeline 9.

The continuously distilling column 2 is connected with the tank 1 via the pipeline 9, and the column top section is connected with the condensing tank 3 via a pipeline 10 and the condenser 4. A pipeline 13 is placed at the bottom section of the continuously distilling column 2 for withdrawing the bottom residue, and connected with the middle plate section of the continuously distilling column 5. Further, a pipeline 12 from the condensing tank 3 is connected with the neighborhood of the column top section of the continuously distilling column 2.

The mixed liquid is continuously fed from the tank 1 to the middle plate section of the continuously distilling column 2 via the pipeline 9. Water is continuously distilled as the distillate. On the other hand, a solution comprising N-vinyl-2-pyrrolidone, N-(2-hydroxyethyl)-2-pyrrolidone and compounds having a higher boiling point than N-vinyl-2-pyrrolidone is withdrawn as the bottom residue. Part of water as the condensate in the condensing tank 3 is refluxed as the refluxed liquid via the pipeline 12 to the neighborhood of the column top section of the continuously distilling column 2.

The condenser 4 is installed at a predetermined position of the pipeline 10, and gas distilling from the continuously distilling column 2 (distillate) is condensed and liquefied there.

The condensing tank 3 is connected with the column top section of the continuously distilling column 2 via the pipeline 10 and the condenser 4. A pipeline 11 and the pipeline 12 are placed at the bottom section of the condensing tank 3 at such a position as enables withdrawal of the distillate. The pipeline 11 is for withdrawing the distillate, and the pipeline 12 is connected with the neighborhood of the column top section of the continuously distilling column 2.

Water as the distillate from the continuously distilling column 2 is continuously fed into the condensing tank 3. Part of the condensed water is continuously refluxed from the condensing tank 3 to the neighborhood of the column top section of the continuously distilling column 2. Water is withdrawn from the bottom of the condensing tank 3 via the pipeline 11.

The continuously distilling column 5 is a fractionating column of N-vinyl-2-pyrrolidone. The middle plate section of the continuously distilling column 5 is connected with the bottom section of the continuously distilling column 2 via the pipeline 13, and the column top section is connected with the condensing tank 6 via a pipeline 14 and the condenser 7. A pipeline 17 for withdrawing the bottom residue is placed at the bottom section of the continuously distilling column 5. Further, a pipeline 16 from the condensing tank 6 is connected with the neighborhood of the column top section of the continuously distilling column 5.

The bottom residue of the continuously distilling column 2 is continuously fed to the middle plate section of the continuously distilling column 5 via the pipeline 13. In the continuously distilling column 5, N-vinyl-2-pyrrolidone is distilled as the distillate, and a liquid comprising N-(2-hydroxyethyl)-2-pyrrolidone and compounds having a higher boiling point than N-vinyl-2-pyrrolidone is withdrawn as the bottom residue.

The condenser 7 is installed at a predetermined position of the pipeline 14, and the gas distilling from the continuously distilling column 5 (distillate) is condensed here to obtain liquid N-vinyl-2-pyrrolidone.

The condensing tank 6 is connected with the column top section of the continuously distilling column 5 via the pipeline 14 and the condenser 7. A pipeline 15 and the pipeline 16 are placed at the bottom section of the condensing tank 7 at such a position as enables withdrawal of the distillate. The pipeline 15 is for withdrawing the distillate, and the pipeline 16 is connected with the neighborhood of the column top section of the continuously distilling column 5.

N-vinyl-2-pyrrolidone as the distillate from the continuously distilling column 5 is continuously fed into the condensing tank 6. Part of the condensed N-vinyl-2-pyrrolidone is continuously refluxed from the condensing tank 6 to the neighborhood of the column top section of the continuously distilling column 5. N-vinyl-2-pyrrolidone is appropriately withdrawn from the bottom of the condensing tank 6 via the pipeline 15.

Besides the above various apparatuses, various accessory apparatuses needed for distillation operation, for example, heat exchangers, pumps, intermediate tanks, etc. are installed in the distilling apparatus, although they are not illustrated.

When the process of the invention is carried out using the thus constructed distilling apparatus, a mixed liquid containing N-vinyl-2-pyrrolidone, N-(2-hydroxyethyl)-2-pyrrolidone, compounds having a higher boiling point than N-vinyl-2-pyrrolidone and water is, first, continuously fed into the tank 1, and also continuously fed from the tank 1 to the middle plate section of the continuously distilling column 2. The mixed liquid fed into the continuously distilling column 2 is continuously distilled, and water is distilled as the distillate from the column top, and a liquid containing N-vinyl-2-pyrrolidone, N-(2-hydroxyethyl)-2-pyrrolidone and compounds having a higher boiling point than N-vinyl-2-pyrrolidone is withdrawn from the bottom as the bottom residue. In this operation, it is pertinent that the temperature of the bottom liquid of the continuously distilling column 2 is 180° C. or less, preferably 165° C. or less. When the temperature of the bottom liquid is more than 180° C., thermal polymerization or thermal decomposition of N-vinyl-2-pyrrolidone in the bottom liquid is accelerated and the recovery percentage of N-vinyl-2-pyrrolidone is lowered. It is pertinent that distillation in the continuously distilling column 2 is carried out under a reduced pressure of $2.66 \times 10^4$ Pa (200 mmHg) or less, preferably $1.99 \times 10^4$ Pa (150 mmHg) or less.

Then, the distillate (water) from the continuously distilling column 2 is condensed in the condenser 4 and continuously fed into the condensing tank 3. This distillate (water) is continuously refluxed to the neighborhood of the column top of the continuously distilling column 2 via the pipeline 12, and at the same time, appropriately withdrawn from the bottom section of the condensing tank 3 via the pipeline 11.

Other distillation conditions in the continuously distilling column 2, for example, the plate number of the column, reflux ratio, etc. are not particularly limited.

The bottom residue from the continuously distilling column 2 is continuously fed to the middle plate section of the continuously distilling column 5 via the pipeline 13. The fed bottom residue is continuously distilled, and N-vinyl-2-pyrrolidone is distilled as the distillate from the column top, and the residual N-(2-hydroxyethyl)-2-pyrrolidone and the compounds having a higher boiling point than N-vinyl-2-pyrrolidone are withdrawn as the bottom residue from the bottom. In the continuously distilling column 5, the temperature of the bottom liquid should be controlled to 230° C. or less, preferably 210° C. or less. By controlling the temperature of the bottom liquid to 230° C. or less, thermal decomposition of N-vinyl-2-pyrrolidone in the distilling column is inhibited. It is preferable that the distillation in the continuously distilling column 5 is carried out under a reduced pressure of $1.33 \times 10^4$ Pa (100 mmHg) or less, particularly $0.66 \times 10^4$ Pa (50 mmHg) or less.

The distillate (N-vinyl-2-pyrrolidone) from the continuously distilling column 5 is condensed in the condenser 7, and continuously fed into the condensing tank 6. This distillate (N-vinyl-2-pyrrolidone) is continuously refluxed to the neighborhood of the column top of the continuously distilling column 5 via the pipeline 16, and at the same time, appropriately withdrawn from the bottom section of the condensing tank 6 via the pipeline 15. Thus by refluxing section of N-vinyl-2-pyrrolidone from the condensing tank 6 into the continuously distilling column 5, the effect of reflux operation can be obtained. Other distillation conditions in the continuously distilling column 5, for example, the plate number of the column, reflux ratio, etc. are not particularly limited.

By carrying out the above distillation operations, it is possible to recover N-vinyl-2-pyrrolidone continuously and steadily and in high purity from the mixed liquid containing N-vinyl-2-pyrrolidone, N-(2-hydroxyethyl)-2-pyrrolidone, compounds having a higher boiling point than N-vinyl-2-pyrrolidone and water, without being accompanied by thermal polymerization or thermal decomposition of N-vinyl-2-pyrrolidone. In addition, N-(2-hydroxyethyl)-2-pyrrolidone can easily be recovered by further distilling the bottom residue of the continuously distilling column 5, and the recovered N-(2-hydroxyethyl)-2-pyrrolidone is recycled for example in the N-vinyl-2-pyrrolidone-preparing apparatus, etc.

It goes without saying that continuously distilling columns used in the recovery of N-vinyl-2-pyrrolidone according to the process of the invention are not limited only to those of the construction shown in FIG. 1.

EXAMPLE

The invention is further specifically described below according to examples, but the invention should not be limited thereto at all.

Example 1

N-vinyl-2-pyrrolidone was continuously recovered using an apparatus showing in FIG. 1.

As the continuously distilling column 2 was used a glass tube of inside diameter 35 mm into which stainless steel-made Suluzer packing of diameter 35 mm was packed as packing at the enriching section in 4 elements and at the stripping section in 6 elements. As the continuously distilling column 5 was used a glass tube of inside diameter 50 mm into which stainless steel-made Suluzer packing of diameter 50 mm was packed as packing at the enriching section in 7 elements and at the stripping section in 7 elements. The temperatures of the condensates in the condensing tanks 3 and 6 were maintained at 10° C.

The continuously distilling column 2 was operated under a reduced pressure of $1.33\times10^4$ Pa (100 mmHg) controlling the amount of the condensate refluxed from the condensing tank 3 into the continuously distilling column 2 so that the reflux ratio could be 0.5. The continuously distilling column 5 was operated under a reduced pressure of $1.33\times10^3$ Pa (10 mmHg) controlling the amount of the condensate refluxed from the condensing tank 6 into the continuously distilling column 5 so that the reflux ratio could be 1.

The feed amount per unit time of the mixed liquid fed from the tank 1 into the continuously distilling column 2 (hereinafter, referred to as feed speed), the distillation amount per unit time of the distillate from the continuously distilling column 2 (hereinafter, referred to as distillation speed), the withdrawal amount per unit time of the bottom residue from the continuously distilling column 2 (hereinafter, referred to as withdrawal speed), the feed speed of the bottom residue to the continuously distilling column 5, the distillation speed of the distillate from the continuously distilling column 5 and the withdrawal speed of the bottom residue from the continuously distilling column 5 are shown together with the compositions of the respective liquids in Table 1. In Table 1, "NVP", "2-Py", "HEP" and "High boiling compounds" mean N-vinyl-2-pyrrolidone, 2-pyrrolidone, N-(2-hydroxyethyl)-2-pyrrolidone, and compounds other than 2-pyrrolidone having a higher boiling point than N-vinyl-2-pyrrolidone, respectively. The column top temperatures and bottom liquid temperatures of the continuously distilling columns 2 and 5 are shown in Table 2.

TABLE 1

| | Composition | | | | |
|---|---|---|---|---|---|
| | Water (g/h) | NVP (g/h) | 2-Py (g/h) | HEP (g/h) | High boiling compounds (g/h) |
| Continuously distilling column 2 | | | | | |
| Feed speed | 37.7 | 232.5 | 1.8 | 119.4 | 5.7 |
| Distillation speed | 37.7 | 0 | 0 | 0 | 0 |
| Withdrawal speed | 0 | 227.8 | 1.8 | 119.4 | 10.4 |
| Continuously distilling column 5 | | | | | |
| Feed speed | 0 | 227.8 | 1.8 | 119.4 | 10.4 |
| Distillation speed | 0 | 223.3 | 0.1 | 0.1 | 0 |
| Withdrawal speed | 0 | 0 | 1.7 | 119.3 | 14.9 |

TABLE 2

| | Continuously distilling column 2 | Continuously distilling column 5 |
|---|---|---|
| Column top temperature (° C.) | 52 | 89 |
| Bottom liquid temperature (° C.) | 160 | 195 |

It is understood from the values shown in Table 1 that, in the continuously distilling column 2, water in the mixed liquid is distilled as the distillate and, on the other hand, the residual components are withdrawn as the bottom residue. Further, it is understood that, in the continuously distilling column 5, the desired compound N-vinyl-2-pyrrolidone is distilled as the distillate.

Thus, it is apparent that N-vinyl-2-pyrrolidone is continuously recovered by the recovery process according to the invention.

Further, the ratio of the amount of N-vinyl-2-pyrrolidone withdrawn as the bottom residue from the continuously distilling column 2 to the feed amount of N-vinyl-2-pyrrolidone into the continuously distilling column 2, namely, the recovery percentage of N-vinyl-2-pyrrolidone in the continuously distilling column 2 was 98% by weight. The ratio of the distillation amount of N-vinyl-2-pyrrolidone from the continuously distilling column 5 to the feed amount of N-vinyl-2-pyrrolidone into the continuously distilling column 5, namely the recovery percentage of N-vinyl-2-pyrrolidone in the continuously distilling column 5 was 98% by weight. Therefore, the ratio of the distillation amount of N-vinyl-2-pyrrolidone from the continuously distilling column 5 to the feed amount of N-vinyl-2-pyrrolidone into the continuously distilling column 2, namely the recovery percentage of N-vinyl-2-pyrrolidone was 96% by weight. And, the purity of the recovered N-vinyl-2-pyrrolidone was 99.9% by weight.

Example 2

N-vinyl-2-pyrrolidone was continuously recovered using an apparatus shown in FIG. 1. The constructions of the continuously distilling column 2 and the continuously distilling column 5 were the same as in Example 1, and the temperatures of the condensates in the condensing tanks 3 and 6 were maintained at 10° C.

The continuously distilling column 2 was operated under a reduced pressure of $1.33\times10^4$ Pa (100 mmHg) controlling the amount of the condensate refluxed from the condensing tank 3 into the continuously distilling column 2 so that the reflux ratio could be 1. The continuously distilling column 5 was operated under a reduced pressure of $1.33\times10^3$ Pa (10 mmHg) controlling the amount of the condensate refluxed from the condensing tank 6 into the continuously distilling column 5 so that the reflux ratio could be 1.5.

The feed speed, distillation speed and withdrawal speed on each of the continuously distilling column 2 and the continuously distilling column 5 are shown, together with the composition of each liquid, in Table 3, and the column top temperature and the bottom liquid temperature of each of the continuously distilling columns 2 and 5 are shown in Table 4.

TABLE 3

| | Composition | | | | |
|---|---|---|---|---|---|
| | Water (g/h) | NVP (g/h) | 2-Py (g/h) | HEP (g/h) | High boiling compounds (g/h) |
| Continuously distilling column 2 | | | | | |
| Feed speed | 24.8 | 153.4 | 1.2 | 273 | 2 |
| Distillation speed | 24.8 | 0 | 0 | 0 | 0 |
| Withdrawal speed | 0 | 148.8 | 1.2 | 273 | 6.6 |
| Continuously distilling column 5 | | | | | |
| Feed speed | 0 | 148.8 | 1.2 | 273 | 6.6 |
| Distillation speed | 0 | 145.8 | 0.1 | 0.1 | 0 |
| Withdrawal speed | 0 | 0 | 1.1 | 272.9 | 9.6 |

TABLE 4

|  | Continuously distilling column 2 | Continuously distilling column 5 |
|---|---|---|
| Column top temperature (° C.) | 52 | 89 |
| Bottom liquid temperature (° C.) | 178 | 205 |

It is understood from the values shown in Table 3 that, in the continuously distilling column 2, water in the mixed liquid is distilled as the distillate and, on the other hand, the residual components are withdrawn as the bottom residue. Further, it is understood that, in the continuously distilling column 5, the entire N-vinyl-2-pyrrolidone in the mixed liquid was distilled as the distillate.

Thus, it is apparent that N-vinyl-2-pyrrolidone is continuously recovered by the recovery process according to the invention.

Further, the ratio of the amount of N-vinyl-2-pyrrolidone withdrawn as the bottom residue from the continuously distilling column 2 to the feed amount of N-vinyl-2-pyrrolidone into the continuously distilling column 2, namely, the recovery percentage of N-vinyl-2-pyrrolidone in the continuously distilling column 2 was 97% by weight. The ratio of the distillation amount of N-vinyl-2-pyrrolidone from the continuously distilling column 5 to the feed amount of N-vinyl-2-pyrrolidone into the continuously distilling column 5, namely the recovery percentage of N-vinyl-2-pyrrolidone in the continuously distilling column 5 was 98% by weight. Therefore, the ratio of the distillation amount of N-vinyl-2-pyrrolidone from the continuously distilling column 5 to the feed amount of N-vinyl-2-pyrrolidone into the continuously distilling column 2, namely the recovery percentage of N-vinyl-2-pyrrolidone was 95% by weight. And, the purity of the recovered N-vinyl-2-pyrrolidone was 99.9% by weight.

Comparative Example 1

N-vinyl-2-pyrrolidone was continuously recovered using an apparatus shown in FIG. 1. The constructions of the continuously distilling column 2 and the continuously distilling column 5 were the same as in Example 1, and the temperatures of the condensates in the condensing tanks 3 and 6 were maintained at 10° C.

The continuously distilling column 2 was operated under a reduced pressure of $3.33 \times 10^4$ Pa (250 mmHg) controlling the amount of the condensate refluxed from the condensing tank 3 into the continuously distilling column 2 so that the reflux ratio could be 0.5. The continuously distilling column 5 was operated under a reduced pressure of $1.33 \times 10^3$ Pa (10 mmHg) controlling the amount of the condensate refluxed from the condensing tank 6 into the continuously distilling column 5 so that the reflux ratio could be 1.

The feed speed, distillation speed and withdrawal speed on each of the continuously distilling column 2 and the continuously distilling column 5 are shown, together with the composition of each liquid, in Table 5, and the column top temperature and the bottom liquid temperature of each of the continuously distilling columns 2 and 5 are shown in Table 6.

TABLE 5

| | Composition | | | | |
|---|---|---|---|---|---|
| | Water (g/h) | NVP (g/h) | 2-Py (g/h) | HEP (g/h) | High boiling compounds (g/h) |
| Continuously distilling column 2 | | | | | |
| Feed speed | 37.7 | 232.5 | 1.8 | 119.4 | 5.7 |
| Distillation speed | 37.7 | 0 | 0 | 0 | 0 |
| Withdrawal speed | 0 | 209.3 | 1.8 | 19.4 | 28.9 |
| Continuously distilling column 5 | | | | | |
| Feed speed | 0 | 209.3 | 1.8 | 119.4 | 28.9 |
| Distillation speed | 0 | 205.1 | 0.2 | 0.1 | 0 |
| Withdrawal speed | 0 | 0 | 1.6 | 119.3 | 33.1 |

TABLE 6

|  | Continuously distilling column 2 | Continuously distilling column 5 |
|---|---|---|
| Column top temperature (° C.) | 72 | 89 |
| Bottom liquid temperature (° C.) | 190 | 195 |

It is understood from the values shown in Table 5 that, in the continuously distilling column 2, water in the mixed liquid is distilled as the distillate and, on the other hand, the residual components are withdrawn as the bottom residue. Further, it is understood that, in the continuously distilling column 5, the entire N-vinyl-2-pyrrolidone in the mixed liquid was distilled as the distillate.

However, the ratio of the amount of N-vinyl-2-pyrrolidone withdrawn as the bottom residue from the continuously distilling column 2 to the feed amount of N-vinyl-2-pyrrolidone into the continuously distilling column 2, namely, the recovery percentage of N-vinyl-2-pyrrolidone in the continuously distilling column 2 was 90% by weight. The ratio of the distillation amount of N-vinyl-2-pyrrolidone from the continuously distilling column 5 to the feed amount of N-vinyl-2-pyrrolidone into the continuously distilling column 5, namely the recovery percentage of N-vinyl-2-pyrrolidone in the continuously distilling column 5 was 98% by weight. Therefore, the ratio of the distillation amount of N-vinyl-2-pyrrolidone from the continuously distilling column 5 to the feed amount of N-vinyl-2-pyrrolidone into the continuously distilling column 2, namely the recovery percentage of N-vinyl-2-pyrrolidone was 88% by weight. And, the purity of the recovered N-vinyl-2-pyrrolidone was 99.8% by weight.

Comparative Example 2

N-vinyl-2-pyrrolidone was continuously recovered using an apparatus shown in FIG. 1. The constructions of the continuously distilling column 2 and the continuously distilling column 5 were the same as in Example 1, and the temperatures of the condensates in the condensing tanks 3 and 6 were maintained at 10° C.

The continuously distilling column 2 was operated under a reduced pressure of $1.33 \times 10^4$ Pa (100 mmHg) controlling the amount of the condensate refluxed from the condensing tank 3 into the continuously distilling column 2 so that the reflux ratio could be 0.5. The continuously distilling column 5 was operated under a reduced pressure of $1.46 \times 10^4$ Pa (110 mmHg) controlling the amount of the condensate refluxed from the condensing tank 6 into the continuously distilling column 5 so that the reflux ratio could be 1.

The feed speed, distillation speed and withdrawal speed on each of the continuously distilling column 2 and the continuously distilling column 5 are shown, together with the composition of each liquid, in Table 7, and the column top temperature and the bottom liquid temperature of each of the continuously distilling columns 2 and 5 are shown in Table 8.

TABLE 7

| | Composition | | | | |
|---|---|---|---|---|---|
| | Water (g/h) | NVP (g/h) | 2-Py (g/h) | HEP (g/h) | High boiling compounds (g/h) |
| Continuously distilling column 2 | | | | | |
| Feed speed | 37.7 | 232.5 | 1.8 | 119.4 | 5.7 |
| Distillation speed | 37.7 | 0 | 0 | 0 | 0 |
| Withdrawal speed | 0 | 227.8 | 1.8 | 119.4 | 10.4 |
| Continuously distilling column 5 | | | | | |
| Feed speed | 0 | 227.8 | 1.8 | 119.4 | 10.4 |
| Distillation speed | 0 | 202.7 | 0.2 | 0.1 | 0 |
| Withdrawal speed | 0 | 0 | 1.6 | 119.3 | 35.5 |

TABLE 8

| | Continuously distilling column 2 | Continuously distilling column 5 |
|---|---|---|
| Column top temperature (° C.) | 52 | 149 |
| Bottom liquid temperature (° C.) | 160 | 255 |

It is understood from the values shown in Table 7 that, in the continuously distilling column 2, water in the mixed liquid is distilled as the distillate and, on the other hand, the residual components are withdrawn as the bottom residue. Further, it is understood that, in the continuously distilling column 5, the entire N-vinyl-2-pyrrolidone in the mixed liquid was distilled as the distillate.

However, the ratio of the amount of N-vinyl-2-pyrrolidone withdrawn as the bottom residue from the continuously distilling column 2 to the feed amount of N-vinyl-2-pyrrolidone into the continuously distilling column 2, namely, the recovery percentage of N-vinyl-2-pyrrolidone in the continuously distilling column 2 was 98% by weight. The ratio of the distillation amount of N-vinyl-2-pyrrolidone from the continuously distilling column 5 to the feed amount of N-vinyl-2-pyrrolidone into the continuously distilling column 5, namely the recovery percentage of N-vinyl-2-pyrrolidone in the continuously distilling column 5 was 89% by weight. Therefore, the ratio of the distillation amount of N-vinyl-2-pyrrolidone from the continuously distilling column 5 to the feed amount of N-vinyl-2-pyrrolidone into the continuously distilling column 2, namely the recovery percentage of N-vinyl-2-pyrrolidone was 87% by weight. And, the purity of the recovered N-vinyl-2-pyrrolidone was 99.8% by weight.

As apparent from comparison of the above examples and comparative examples, by obeying the recovery process of the invention, it is possible to inhibit thermal polymerization and thermal decomposition of N-vinyl-2-pyrrolidone, and it is possible to recover the N-vinyl-2-pyrrolidone continuously, efficiently and steadily and in high purity.

Effect of the Invention

By using the recovery process of the invention, an effect is produced that N-vinyl-2-pyrrolidone can be recovered continuously, efficiently and steadily and in high purity, while inhibiting thermal polymerization and thermal decomposition of chemically unstable N-vinyl-2-pyrrolidone, from a mixed liquid having a complicated composition containing N-vinyl-2-pyrrolidone, N-(2-hydroxyethyl)-2-pyrrolidone, compounds having a higher boiling point than N-vinyl-2-pyrrolidone and water, for example, a liquid formed by vapor phase dehydration reaction of N-(2-hydroxyethyl)-2-pyrrolidone.

What is claimed is:

1. In a process for recovering N-vinyl-2-pyrrolidone by continuously distilling a mixed liquid containing N-vinyl-2-pyrrolidone, N-(2-hydroxyethyl)-2-pyrrolidone, compounds having a higher boiling point than N-vinyl-2-pyrrolidone and water using a first distilling column, the improvement comprising carrying out the distillation controlling the temperature of a first bottom liquid of the first distilling column to 180° C. or less to make water distill as an overhead distillate and withdrawing the first bottom liquid comprising N-vinyl-2-pyrrolidone, N-(2-hydroxyethyl)-2-pyrrolidone and the compounds having a higher boiling point than N-vinyl-2-pyrrolidone and recovering N-vinyl-2-pyrrolidone from the first bottom liquid.

2. The process for recovering N-vinyl-2-pyrrolidone according to claim 1 wherein the mixed liquid containing N-vinyl-2-pyrrolidone, N-(2-hydroxyethyl)-2-pyrrolidone, the compounds having a higher boiling point than N-vinyl-2-pyrrolidone and water is a liquid obtained by cooling a N-(2-hydroxyethyl)-2-pyrrolidone product obtained by intramolecularly dehydrating N-(2-hydroxyethyl)-2-pyrrolidone in a vapor phase in the presence of a catalyst.

3. The process for recovering N-vinyl-2-pyrrolidone according to claim 2 which comprises continuously distilling the first bottom liquid withdrawn from the first distilling column using a second distilling column to make N-vinyl-2-pyrrolidone distill as the distillate, and withdrawing a second bottom liquid comprising N-(2-hydroxyethyl)-2-pyrrolidone and the compounds having a higher boiling point than N-vinyl-2-pyrrolidone.

4. The process for recovering N-vinyl-2-pyrrolidone according to claim 3 wherein the distillation is carried out controlling the temperature of the second bottom liquid of the second distilling column to 230° C. or less.

5. The process for recovering N-vinyl-2-pyrrolidone according to claim 1 which comprises continuously distilling the first bottom liquid withdrawn from the first distilling column using a second distilling column to make N-vinyl-2-pyrrolidone distill as an overhead distillate, and withdrawing a second bottom liquid comprising N-(2-hydroxyethyl)-2-pyrrolidone and the compounds having a higher boiling point than N-vinyl-2-pyrrolidone.

6. The process for recovering N-vinyl-2-pyrrolidone according to claim 5 wherein the distillation is carried out controlling the temperature of the second bottom liquid of the second distilling column to 230° C. or less.

* * * * *